US00PP11345P

United States Patent [19]

Heims

[11] Patent Number: Plant 11,345

[45] Date of Patent: Apr. 11, 2000

[54] TIARELLA PLANT NAMED 'SPANISH CROSS'

[75] Inventor: Dan M. Heims, Portland, Oreg.

[73] Assignee: Terra Nova Nurseries, Inc., Portland, Oreg.

[21] Appl. No.: 09/073,006

[22] Filed: May 5, 1998

[51] Int. Cl.[7] ..... A01H 5/00

[52] U.S. Cl. ..... Plt./263

[58] Field of Search ..... Plt./263

*Primary Examiner*—Howard J. Locker
*Assistant Examiner*—Wendy A Baker
*Attorney, Agent, or Firm*—Klarquist Sparkman Campbell Leigh & Whinston, LLP

[57] ABSTRACT

A new and distinct hybrid Tiarella plant characterized by highly colored leaves that are deeply cut, and a heavy blooming habit.

2 Drawing Sheets

The present invention relates to a new and distinct hybrid of Tiarella plant which originated as a cross-pollination of Tiarella 'Skeleton Key' and Tiarella 'Dark Eyes' in the Saxifrage family (*Saxifragaceae*).

The new Tiarella plant is a result of a cross-pollination of Tiarella 'Skeleton Key' (pod parent)(unpatented) and Tiarella 'Dark Eyes' (unpatented)(pollen parent) at Terra Nova Nurseries, Inc., in Canby, Oreg. This hybrid was chosen from a large selection of seedlings. Seed and pollen parent plants were retained to observe habit and to compare with their progeny. The new variety has been reproduced only by asexual propagation (division and tissue culture). Each of the progeny exhibits identical characteristics to the original plant and is unlike any Tiarella offered by any American nursery or book known to me as evidenced by the following characteristics:

1. Unique form and foliage shape; and
2. Profuse bloom of good color.

Asexual propagation by division and tissue-culture as done in Canby, Oreg., shows that the foregoing characteristics and distinctions come true to form and are established and transmitted through succeeding propagations.

Figure 1:
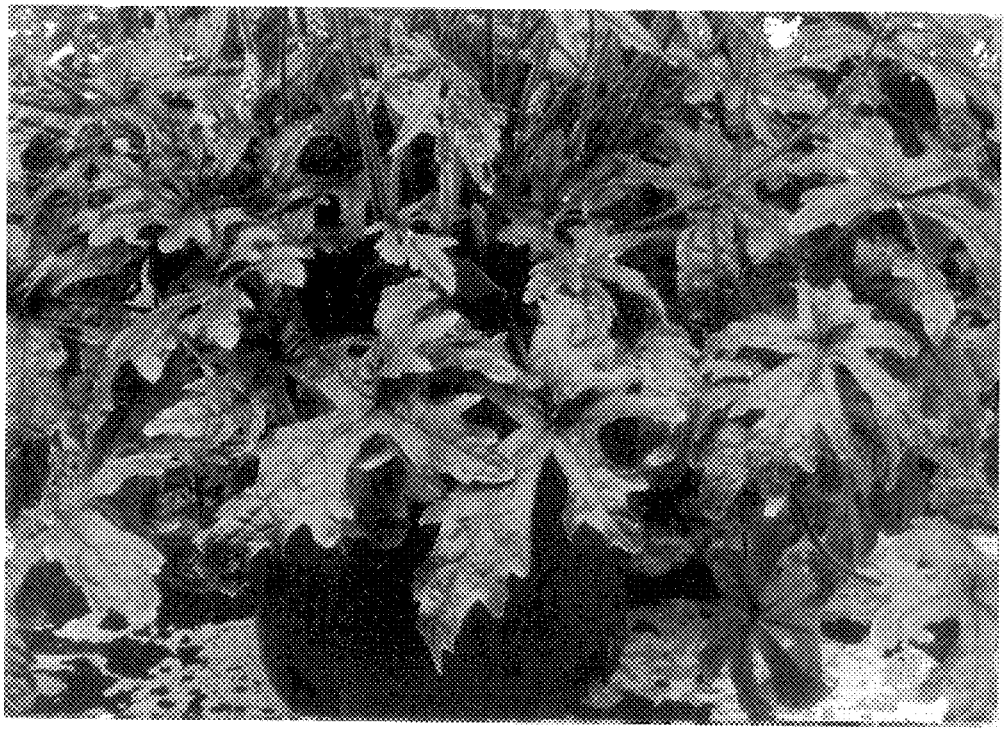
FIG. 1 is a foliage detail of the plant in April.
Figure 2:
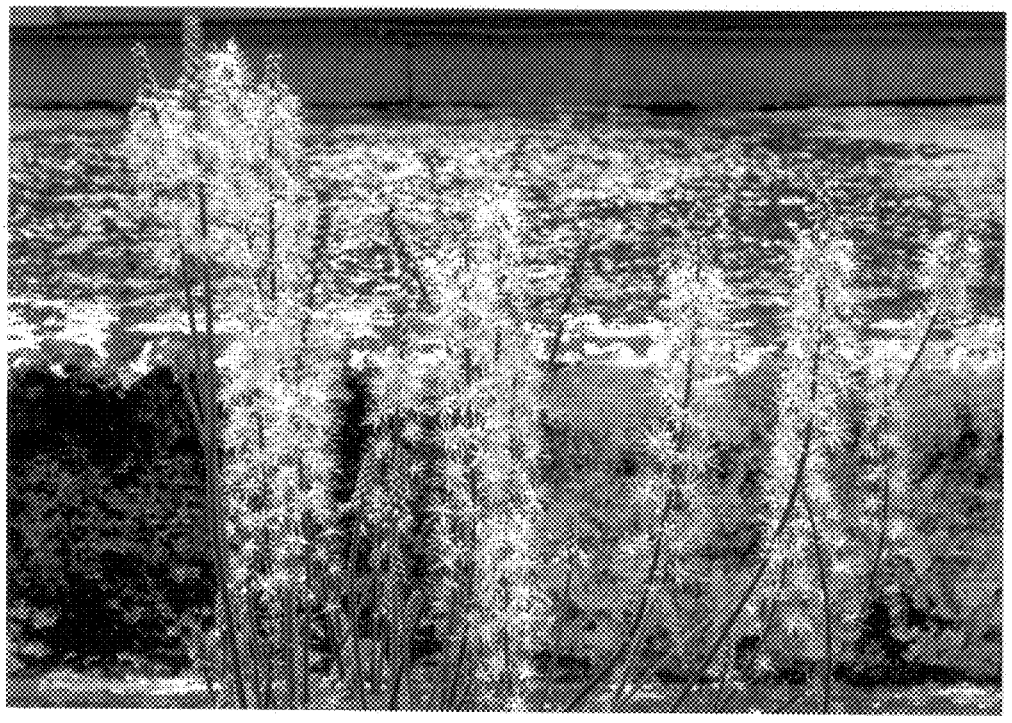
FIG. 2 is a flower scape detail of the plant in April.

The drawings depict the plant as true to type as is photographically possible.

DETAILED PLANT DESCRIPTION

The following is a detailed description of the new Tiarella hybrid based on observations of specimens in Canby, Oreg. The color descriptions are all based on The *Royal Horticultural Society Colour Chart* and *The American Rhododendron Society* publication, "A Contribution Toward Standardization of Color Names in Horticulture."

Foliage:

*Type*.—Semi-evergreen. Evergreen in USDA hardiness zones 5 and above. Herbaceous in USDA hardiness zones 3 and 4.

*Shape*.—Palmate, deeply 5-lobed, irregularly toothed; central lobe elongated, nearly trapezoidal in shape, and irregularly toothed on left half of the trapezoid.

*Length*.—8.7–11. cm (3.5–4.0 in).

*Width*.—6.0–7.5 cm (2.25–3 in).

*Petiole length*.—9–11.5 cm (3.5–4.5 in).

*Margins*.—Deeply toothed.

*Apex*.—Irregularly tridentate with longer central tip.

*Base*.—Hastate.

*Texture*.—Slightly rugose, pilose, light gloss finish.

*Leaf arrangement*.—Basal clump.

*Venation*.—Radiate.

Hardiness: Cold hardy to USDA Zone 3.

Size:

*Height*.—19 cm (2-year-old plant grown in a 2-gal container in Canby, Oreg.).

*Spread*.—38 cm (2-year-old plant grown in a 2-gal container in Canby, Oreg.).

Flower:

*Petal count*.—5 petals, 5 calyx lobes.

*Petal shape*.—Triangular, clawed.

*Flower type*.—Complete, calyx tube campanulate, ovary superior.

*Flower size*.—0.80 cm.

*Flower number*.—40–65 blooms per raceme.

*Flower stem texture*.—Pubescent.

*Flower stem girth*.—1–2 mm.

*Blooming habit*.—Simple upright raceme to 30 cm. Thirty to thirty-five racemes per second-year plant. Some racemes are singly branched. No tendency towards fasciation observed.

*Bloom period*.—April. to May. Minor sporadic rebloom in summer and fall.

Fruit:

*Type*.—Dehiscent capsules.

*Fertilty*.—Fertile.

Color Characteristics:

Foliage:

*Spring/Summer — upper surface*.—R.H.S. 137D–137A Green Group (Moderate Olive Green ARS).

*Spring/Summer — central portion of upper surface*.—R.H.S. 79A Purple Group to R.H.S. 202A Black Group.

*Spring/Summer — upper surface of new growth*.—R.H.S. 148A Yellow-Green Group.

*Spring/Summer — cenral portion of new growth's upper surface and flower stems*.—R.H.S. 185A–187A Greyed Purple Group (Moderate Red ARS).

*Lower surface*.—R.H.S. 191A Greyed-Green Group.

*Lower surface — new growth's lower surface*.—R.H.S. 177A Greyed-Orange Group.

Flowers: Light pink; R.H.S. 36B Red Purple Group. (Light Yellowish Pink ARS).

Habit: Clumping, mounding. This cultivar is not stoloniferous.

DESCRIPTION OF PARENT PLANTS

This Tiarella hybrid has characteristics which make it unique from its parents: Tiarella 'Skeleton Key', a deeply cut-leaved cultivar, and Tiarella 'Dark Eyes', a glossy, heavily blooming cultivar with entire leaves. Both parents are of hybrid origin and were both put into the trade by Terra Nova Nurseries, Inc. Tiarella 'Spanish Cross' has highly colored leaves that are deeply cut, and a heavy blooming habit.

No other Tiarella in commerce resembles Tiarella 'Spanish Cross'.

I claim:

1. A new and distinct hybrid Tiarella plant substantially as shown and described, characterized by highly colored leaves that are deeply cut, and a heavy blooming habit.

* * * * *